United States Patent [19]
Zhang et al.

[11] Patent Number: 5,952,469
[45] Date of Patent: Sep. 14, 1999

[54] MURINE UCP3 POLYPEPTIDES

[75] Inventors: Ning Zhang; M. Catherine Arnaral; Jin-Long Chen, all of South San Francisco, Calif.

[73] Assignee: Tularik Inc., South San Francisco, Calif.

[21] Appl. No.: 09/172,528

[22] Filed: Oct. 14, 1998

Related U.S. Application Data

[62] Division of application No. 08/937,466, Sep. 25, 1997, Pat. No. 5,846,779.

[51] Int. Cl.[6] ..................................................... C07K 14/47
[52] U.S. Cl. .............................................................. 530/350
[58] Field of Search ..................................... 530/300, 324, 530/325, 326, 327, 328, 350; 435/183

[56] References Cited

PUBLICATIONS

Ngo et al, The Protein Folding Problem and Tertiary Structure Prediction, Mertz et al (eds.), pp. 433 and 492–495, Birkhauser, Boston, 1994.

*Primary Examiner*—Terry McKelvey
*Attorney, Agent, or Firm*—Richard Aron Osman

[57] ABSTRACT

The invention provides methods and compositions relating to a novel family of UCP3 polypeptides and related nucleic acids involved in metabolic regulation. The polypeptides may be produced recombinantly from transformed host cells from the disclosed mUCP3 encoding nucleic acids or purified from mammalian cells. The invention provides isolated mUCP3 hybridization probes, knock-out/in constructs and primers capable of specifically hybridizing with the disclosed mUCP3 genes, mUCP3-specific binding agents such as specific antibodies, animals and cells modified with the subject mUCP3 nucleic acids, and methods of making and using the subject compositions in the biopharmaceutical industry.

3 Claims, 6 Drawing Sheets

MVGLQPSEVPPTTVVKFLGAGTAACFADLLTFPLDTAKVRLQIQGENPGA 50

QSVQYRGVLGTILTMVRTEGPRSPYSGLVAGLHRQMSFASIRIGLYDSVK 100

QFYTPKGADHSSVAIRILAGCTTGAMAVTCAQPTDVVKVRFQAMIRLGTG 150

GERKYRGTMDAYRTIAREEGVRGLWKGTWPNITRNAIVNCAEMVTYDIIK 200

EKLLESHLFTDNFPCHFVSAFGAGFCATVVASPVDVVKTRYMNAPLGRYR 250

SPLHCMLKMAAQEGPTAFYKGFVPSFLRLGAWNVMMFVTYEQLKRALMKV 300

QVLRESPF 308

Fig 1

```
GTCAGCTGGT GCACAGGGCC AGTGCCGAGC CAGGGACAGC AGAGACAACA GTGAATGGTG    60
AGGCCCGGCC GTCAGATCCT GCTGCTACCT AATGGAGTGG AGCCTTAGGG TGGCCCTGCA   120
CTACCCAACC TTGGCTAGAC GCACAGCTTC CTCCCTGAAC TGAAGCAAAA GATTGCCAGG   180
CAAGCTCTCT CCTCGGACCT CCATAGGCAG CAAAGGAACC AGGCCCATTC CCCGGGACCA   240
TGGTTGGACT TCAGCCCTCC GAAGTGCCTC CCACAACGGT TGTGAAGTTC CTGGGGGCCG   300
GCACTGCGGC CTGTTTTGCG GACCTCCTCA CTTTTCCCCT GGACACCGCC AAGGTCCGTC   360
TGCAGATCCA AGGGGAGAAC CCAGGGGCTC AGAGCGTGCA GTACCGCGGT GTGCTGGGTA   420
CCATCCTGAC TATGGTGCGC ACAGAGGGTC CCCGCAGCCC CTACAGCGGA CTGGTCGCTG   480
GCCTGCACCG CCAGATGAGT TTTGCCTCCA TTCGAATTGG CCTCTACGAC TCTGTCAAGC   540
AGTTCTACAC CCCCAAGGGA GCGGACCACT CCAGCGTCGC CATCAGGATT CTGGCAGGCT   600
GCACGACAGG AGCCATGGCA GTGACCTGCG CCCAGCCCAC GGATGTGGTG AAGGTCCGAT   660
TTCAAGCCAT GATACGCCTG GGAACTGGAG GAGAGAGGAA ATACAGAGGG ACTATGGATG   720
CCTACAGAAC CATCGCCAGG GAGGAAGGAG TCAGGGGCCT GTGGAAAGGG ACTTGGCCCA   780
```

Fig 2a

```
ACATCACAAG AAATGCCATT GTCAACTGTG CTGAGATGGT GACCTACGAC ATCATCAAGG   840

AGAAGTTGCT GGAGTCTCAC CTGTTTACTG ACAACTCCC  CTGTCACTTT GTCTCTGCCT   900

TTGGAGCTGG CTTCTGTGCC ACAGTGGTGG CCTCCCCGGT GGATGTGGTA AAGACCCGAT   960

ACATGAACGC TCCCCTAGGC AGGTACCGCA GCCCTCTGCA CTGTATGCTG AAGATGGCGG  1020

CTCAGGAGGG ACCCACGGCC TTCTACAAAG GATTGTGCC  CTCCTTTCTG CGTCTGGGAG  1080

CTTGGAACGT GATGATGTTT GTAACATATG AGCAACTGAA GAGGGCCTTA ATGAAAGTCC  1140

AGGTACTGCG GGAATCTCCG TTTTGAACAA GGCAAGCAGG CTGCCTGAAA CAGAACAAAG  1200

CGTCTCTGCC CTGGGGACAC AGGCCCACAC GGTCCAAAAC CCTGCACTGC TGCTGACACG  1260

AGAAACTGAA CTAAAAGAGG AGAGTTTTAG TCCTCCGTGT TTCGTCCTAA AACACCTCTG  1320

TTTGCACTG  ACCTGATGGG AAATAAATTA TATTAATTTT TAAACCCCTT CCGGTTGGAT  1380

GCCTAATATT TAGGCAAGAG ACAACAAAGA AAACCAGAGT CAACTCCCTT GAAATGTAGG  1440

AATAAAGGAT GCATAATAAA CAGGAAAGGC ACAGGTTTTG AGAAGATCAG CCCACAGTGT  1500

TGTCCCTTGAA TCAAACAAAA TGGTCGGAGG AACCCTTCGG CTTCAGCACA AAGAGGTGAC  1560
```

Fig 2b

```
TACAGCCTTC TGGTCACCAG ATGACTCCGC CCCTCTGTAA TGAGTCTGCC AAGTAGACTC  1620
TATCAAGATT CTGGGGAAAG GAGAAAGAAC ACATTGATAC TGCACAAATG AGTGGTGCTG  1680
GGCCCACCGA GGACACTGGA GGATGGAGCG TGATCTGGGA TAACAGTCCT TCTCTGTCTG  1740
CCTCATCAGG GTGTTGGGAA GATAGAAAGC GAAGCAGACA TGGAAGCACT TCCTAACAAG  1800
GCCTGTCATC GTCATCATCT ACAAATGTAA GCCTGAGGAC AATGTTTTAG GAGAGATTCT  1860
GTCCAGAGAA GTAGTTTGAG GAAAATGCAG TTTGTAGTGG TAAAGCCATG CACACCTGGA  1920
CTGCATGGTA AGGACCAGGG GTGACGGAAG CCATGGGGAT CCGGTGCCTG GTAACATCAA  1980
AGGGCTGTGG GGGGGGGGGG GCACTGCCTG TCCATCAGTT CAAAGCAGCA GGACTCAGAA  2040
TCTCCACCTT AGGGCAAGAA CGAGAACAGC TGCTCTCTCT CCTTCTCTCT CGGAGGTTTT  2100
CTCATCTCAG GGTCCTACCT GCCAGGCTCC TGACCAGCTC CACCTGCCCA CACTTCCTCC  2160
TGCTCTCGCT GCCTTTGGCT GCAGAGCCTT TGCTCCTCCT GTTAAGCCTT CAGTCTTCCA  2220
TCTGCAAAAG GGAGGGCAAA GCACAGGACC AACTTCCAAG CTTAAAAATG CACATCTGAC  2280
AACAAAATGG CTCAGTGGGG TCCATTCATG GGACCCACAT GGTGGAAGGA CAGAATGGAC  2340
```

Fig 2c

```
TCTTGCAAAT TGTCCTCTGA CCTCCATTTG AGCGCCCTAT ACATGTGACT GTACATATGT   2400
ACAAACACGA TAAAGATGGA AACACATGTA AAAACATAAA AATAAAAAGT TGTACTGGAT   2460
GTGGTGGTTT GAATGAGATG TTCCTCGTGT CTCGGGCATT TGAAGACTTG CTCCCCAGTT   2520
GTTGGCGGCT GTTTGGGGAG GCTTAGAAGA TGTGGCCTTT TGGGAAGCAG GGTGTCATTG   2580
AGGACTGGCT TGGAGAGCCT AAAGATCCGA GGCACTCCCA GTTTCTCTGG TTTTTCATTT   2640
TGAGGTGTGA GGTCTTATTG GCTGCACCAG TCTCCATGCC TGTCTGTTGC CCGGCCTCCT   2700
CACCATGATG GACTTTTATC TCTCTGTACT TGTAAGCCCC AATAAACCT TCCATCTGTG    2760
AAAAAAAAAA AAAAAAAAAA AA                                            2782
```

MURINE UCP3 POLYPEPTIDES

CROSS-REFERENCE TO RELATED APPLICATION

This application is a divisional application of and claims priority under 35USC120 to U.S. application Ser. No. 08/937,466, filed on Sep. 25, 1997 (now U.S. Pat. No. 5,846,779).

FIELD OF THE INVENTION

The field of this invention is UCP3 genes and their use in biotechnology.

BACKGROUND

A mitochondrial protein called uncoupling protein (UCP1) is thought to play an important role in the body's regulation of energy utilization. Such regulation provides wide spread physiological controls including body weight, appetite, glucose metabolism, temperature, immune responses, etc. Mechanistically, UCP1 is thought to create a pathway that allows dissipation of the proton electrochemical gradient across the inner mitochondrial membrane in brown adipose tissue, without coupling to any other energy consuming process (for review, see Nicholis & Locke (1984) Physiol Rev 64, 1–64). Unfortunately, the role of UCP 1 in physiologies such as body weight regulation in large adult mammals such as people, cattle, pigs, etc. is likely to be limited, since there is little brown adipose tissue in such animals.

UCP2 is a second, related uncoupling protein that is much more widely expressed in large adult mammals (see, e.g. Fleury et al. (1997) Nature Genetics 15, 269–272 and Tartaglia et al. (1996) WO96/05861). Consistent with a role in the regulation of energy utilization generally, and in diabetes and obesity in particular, the UCP2 gene is upregulated in response to fat feeding and maps to regions of the human and mouse genomes linked to hyperinsulinaemia and obesity. More recently, a third structurally related UCP gene, hUCP3 has been charaterized and found to be preferentially expressed in skeletal muscle and brown adipose tissues; see, Vidal-Puig et al. (1997) BBRC 235, 79–82 and Boss et al. (1997) FEBS Letters 408, 39–42.

SUMMARY OF THE INVENTION

The invention provides methods and compositions relating to isolated mUCP3 polypeptides, related nucleic acids, polypeptide domains thereof having mUCP3-specific structure and activity and modulators of mUCP3 function. mUCP3 polypeptides and modulators of mUCP3 expression and/or function can regulate mitochodrial respiration and hence provide important regulators of cell metabolism and function. The polypeptides may be produced recombinantly from transformed host cells or extracts from the subject mUCP3 polypeptide encoding nucleic acids or purified from mammalian cells. The invention provides isolated mUCP3 hybridization probes and primers capable of specifically hybridizing with the disclosed mUCP3 genes, mUCP3-specific binding agents such as specific antibodies, and methods of making and using the subject compositions in diagnosis (e.g. genetic hybridization screens for mUCP3 transcripts) and in the biopharmaceutical industry (e.g. as immunogens, reagents for isolating other transcriptional regulators, knockin/out vectors, transgenic animals anc cell lines, reagents for screening chemical libraries for lead pharmacological agents, etc.).

BRIEF DESCRIPTION OF THE FIGURES

FIG. 1 shows the amino acid sequence of a mUCP3a polypeptide (SEQ ID NO:2), indicating mUCP3a-specific sequences and domains in common with hUCP3.

FIGS. 2a–2d show the nucleotide sequence of a mUCP3a-encoding cDNA (SEQ ID NO: 1), indicating mUCP3a-specific sequences and domains in common with hUCP3.

DETAILED DESCRIPTION OF THE INVENTION

Figure 3:
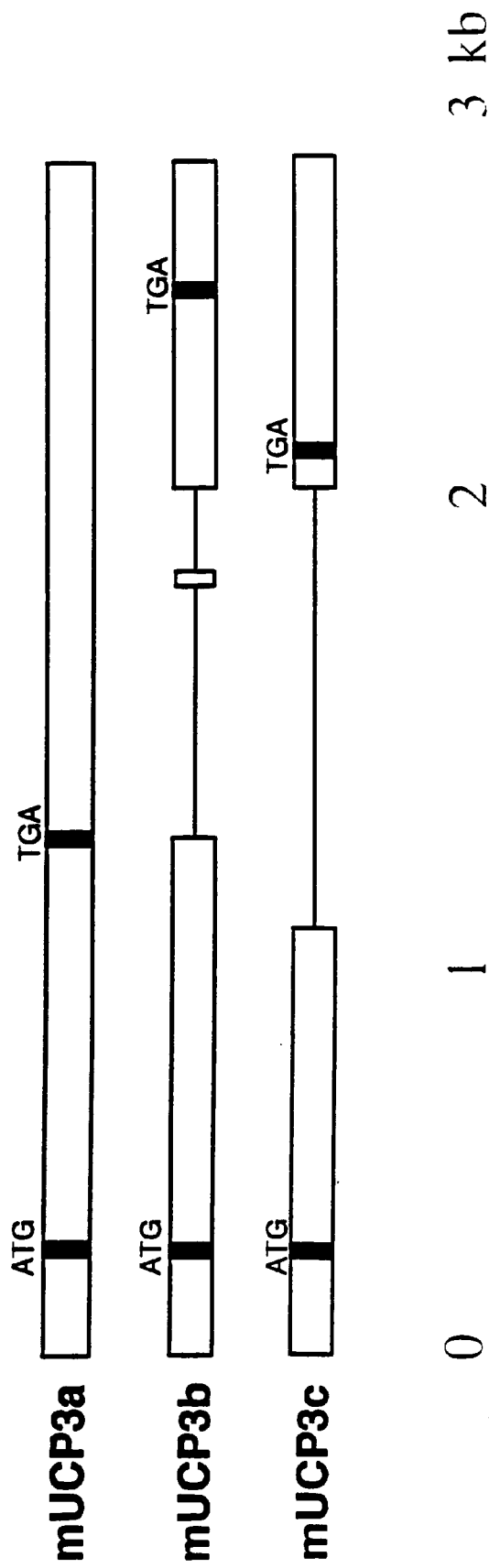
FIG. 3 shows the structures of mUCP3 isoforms a, b and c.

Exemplary nucleotide sequences of natural cDNAs encoding mUCP3 polypeptides are shown as SEQ ID NO: 1, 3 and 5, and their full conceptual translates are shown as SEQ ID NOS:2, 4 and 6, respectively. The mUCP3 polypeptides of the invention include incomplete translates of SEQ ID NOS: 1, 3 and 5 which translates and deletion mutants of SEQ ID NOS:2, 4 and 6 have mUCP3-specific amino acid sequence, binding specificity or function. Preferred translates/deletion mutants comprise at least a 6, preferably at least an 8, more preferably at least a 10, most preferably at least a 12 residue domain of the translates not found in hUCP3. Such domains are readily discernable from alignments of mUCP3 polypeptides and hUCP3. See, e.g. FIG. 1 for the mUCP3a amino acid domains in common (bold) and not in common with hUCP3 and FIGS. 2a–2d for the mUCP3a nucleic acid domains in common (bold) and not in common with the nucleic acid domains of hUCP3.

The subject domains provide mUCP3 domain specific activity or function which are conveniently determined in vitro, cell-based, or in vivo assays: e.g. in vitro binding assays, cell culture assays, in animals (e.g. gene therapy, transgenics, etc.), etc. mUCP3-binding specificity may assayed by binding equilibrium constants (usually at least about $10^7$ $M^{-1}$, preferably at least about $10^8$ $M^{-1}$, more preferably at least about $10^9$ $M^{-1}$), by the ability of the subject polypeptide to function as negative mutants in mUCP3-expressing cells, to elicit mUCP3 specific antibody in a heterologous host (e.g a rabbit), etc. In any event, the mUCP3 binding specificity of the subject mUCP3 polypeptides necessarily distinguishes that of hUCP3. Preferred peptides demonstrate mUCP3 domain specific activity as assayed by respiratory uncoupling activity, ATP-binding or binding inhibitory activity, mUCP3-specific antibody binding, etc. For example, mUCP3 domain peptides with assay demonstrable mUCP3 domain-specific activities include: SEQ ID NO:2, residues 3–12; SEQ ID NO:2, residues 37–58; SEQ ID NO:2, residues 100–115; SEQ ID NO:2, residues 144–158; SEQ ID NO:2, residues 182–198; SEQ ID NO:2, residues 198–209 SEQ ID NO:2, residues 242–266; SEQ ID NO:2, residues 268–290; and SEQ ID NO:2, residues 297–308.

The subject mUCP3 polypeptides are isolated or pure: an "isolated" polypeptide is unaccompanied by at least some of the material with which it is associated in its natural state. Isolated polypeptides encompass UCP3 polypeptides covalently joined to a non-natural or heterologous component, such as a non-natural amino acid or amino acid sequence or a natural amino acid or sequence other than that which the polypeptide is joined to in a natural protein, and preferably constitutes at least about 0.5%, and more preferably at least about 5% by weight of the total polypeptide in a given sample and a pure polypeptide constitutes at least about 90%, and preferably at least about 99% by weight of the total polypeptide in a given sample. A polypeptide, as used herein, is an polymer of amino acids, generally at least 6 residues, preferably at least about 10 residues, more preferably at least about 25 residues, most preferably at least about 50 residues in length. The mUCP3 polypeptides and polypeptide domains may be synthesized, produced by recombinant technology, or purified from mammalian, preferably murine cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

For example, the invention provides a method of making a polypeptide comprising the steps of introducing an isolated or recombinant nucleic acid encoding a subject polypeptide into a host cell or cellular extract, incubating said host cell or extract under conditions whereby said nucleic acid is expressed as a transcript and said transcript is expressed as a translation product comprising said polypeptide, and isolating said translation product.

The invention provides binding agents specific to the claimed mUCP3 polypeptides, including substrates, agonists, antagonists, natural intracellular binding targets, etc., methods of identifying and making such agents, and their use in pharmaceutical development. Novel mUCP3-specific binding agents include mUCP3-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate mUCP3 function, e.g. mUCP3-dependent respiratory coupling.

Accordingly, the invention provides methods for modulating respiration involving an mUCP3 gene product comprising the step of modulating mUCP3 activity, e.g. by contacting the cell with an mUCP3-specific binding agent. The cell may reside in culture or in situ, i.e. within the natural host. Preferred inhibitors are orally active in mammalian hosts. For diagnostic uses, the inhibitors or other mUCP3 binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed mUCP3 polypeptides are used to back-translate mUCP3 polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural mUCP3-encoding nucleic acid sequences ("GCG" software, Genetics Computer Group, Inc, Madison Wis.). mUCP3-encoding nucleic acids used in mUCP3-expression vectors and incorporated into recombinant host cells, e.g. for expression and screening, transgenic animals, e.g. for functional studies such as the efficacy of candidate drugs for disease associated with mUCP3-modulated cell function, etc.

The invention also provides nucleic acid hybridization probes, knockin/out constructs and replication/amplification primers having a mUCP3 CDNA specific sequence comprising SEQ ID NOS:1, 3 and 5, or fragments thereof, and sufficient to effect specific hybridization thereto (i.e. specifically hybridize with SEQ ID NOS:1, 3 and 5 in the presence of the UCP1, UCP2 and hUCP3 cDNA. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. mUCP3 nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NOS:1, 3 and 5, or fragments thereof contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, knock in/out constructs etc.; use in detecting the presence of mUCP3 genes and gene transcripts and in detecting or amplifying nucleic acids encoding additional mUCP3 homologs and structural analogs. In diagnosis, mUCP3 hybridization probes find use in identifying wild-type and mutant mUCP3 alleles in clinical and laboratory samples. In a particular embodiment, mUCP3 nucleic acids are used to modulate cellular expression or intracellular concentration or availability of active mUCP3 by binding and/or recombining with an endogenous mUCP3 gene or gene transcript. Methods for effecting anti-sense hyridization, homologous and non-homologous recombinations, and generating transgenic animals and cell lines are well-established in the art.

The following experimental section and examples are offered by way of illustration and not by way of limitation.

EXAMPLES

1. Cloning of mUCP3 cDNAs

We searched murine EST databases using human UCP2 cDNA sequence to identify a cDNA with sequence similarity to known human and mouse UCP2 cDNA sequences. Isolated, cloning and sequencing of this clone revealed a novel gene designated mUCP3, with greatest sequence similarity to a human UCP3 gene. Since the clone lacked the 5' end UTR and part of the coding sequence, we designed a primer for 5' end RACE of the cDNA sequence using mouse skeletal muscle cDNA (PCR condition: 95° C., 40 sec, 55° C. 2 min, 72° C., 3 min for 30 cycles). Several clones from the RACE PCR contain sequences that overlap with the partial cDNA sequence. A EcoRI tagged forward primer and XbaI tagged reverse primer were used to amplify the full mUCP3 cDNA using mouse skeletal muscle cDNA. A 2.8 kb mUCP3 cDNA was amplified and cloned into pBlue-Script SK. Several smaller fragments (1.5–2 kb) detected in the PCR products in lesser quantities were also cloned and DNA sequencing confirmed that they were alternatively spliced forms of mUCP3 cDNA.

The largest mUCP3 cDNA (mUCP3a) is 2,782 bp long, containing 239 bp 5' end untranslated region, a 816 bp ORF and 1.7 kb 3' end UTR. The mRNA transcript is about 2.8 kb and the translation product contains 308 amino acid residues. It is 85% identical to the hUCP3 and 73% and 54% identical to mUCP2 and mUCP1, respectively, indicating a similar functional roles in uncoupling mitochondrial respiration. Two shorter isoforms, mUCP3b and mUCP3c are 1,949 bp and 1,777 bp, with translation products of 432 and 256 amino acid residues respectively (see, FIG. 3).

2. Expression of mUCP3 cDNAs

Because of the extensive DNA sequence homology between our mUCP3 genes and mUCP2, we designed a set of primers designed for PCR amplification of a 335 bp mUCP3 specific DNA sequence and cloned into pBlue-Script SK. The cloned fragment was labeled through reverse transcription using a T3/T7 Reverse Transcription Kit from Ambion and used as a probe for Northern blot analysis of mUCP3 expression. The mouse multiple tissue blots were purchased from Clontech and Northern analysis was performed using a Northern Max kit purchased from Ambion. Northern analysis revealed specific enhanced expression in heart and especially skeletal muscle tissues as compared with negligble expression in brain, spleen, lung, liver, kidney and testis tissues.

3. Protocol for high throughput mUCP3a—antibody binding assay.

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.

$^{33}$P mUCP3a polypeptide 10× stock: $10^{-8}$–$10^{-6}$ M "cold" mUCP3 supplemented with 200,000–250,000 cpm of labeled mUCP3a (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.

mUCP3-specific antibody: $10^{-7}$–$10^{-5}$ M biotinylated antibody in PBS.

B. Preparation of assay plates:

Coat with 120 $\mu$l of stock N-Avidin per well overnight at 4° C.

Wash 2 times with 200 $\mu$l PBS.

Block with 150 $\mu$l of blocking buffer.

Wash 2 times with 200 $\mu$l PBS.

C. Assay:

Add 40 $\mu$l assay buffer/well.

Add 10 $\mu$l compound or extract.

Add 10 $\mu$l $^{33}$P-mUCP3a (20–25,000 cpm/0.1–10 pmoles/well=$10^{-9}$–$10^{-7}$ M final cone).

Shake at 25° C. for 15 minutes.

Incubate additional 45 minutes at 25° C.

Add 40 $\mu$M biotinylated antibody (0.1–10 pmoles/40 $\mu$l in assay buffer)

Incubate 1 hour at room temperature.

Stop the reaction by washing 4 times with 200 $\mu$M PBS.

Add 150 $\mu$M scintillation cocktail.

Count in Topcount.

D. Controls for all assays (located on each plate):

a. Non-specific binding b. Soluble (non-biotinylated antibody) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising the amino acid sequence of SEQ ID NO:2.

2. An isolated polypeptide comprising the amino acid sequence of SEQ ID NO:4.

3. An isolated polypeptide comprising the amino acid sequence of SEQ ID NO:6.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2782 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

-continued

```
GTCAGCTGGT GCACAGGGCC AGTGCCGAGC CAGGGACAGC AGAGACAACA GTGAATGGTG      60

AGGCCCGGCC GTCAGATCCT GCTGCTACCT AATGGAGTGG AGCCTTAGGG TGGCCCTGCA     120

CTACCCAACC TTGGCTAGAC GCACAGCTTC CTCCCTGAAC TGAAGCAAAA GATTGCCAGG     180

CAAGCTCTCT CCTCGGACCT CCATAGGCAG CAAAGGAACC AGGCCCATTC CCCGGGACCA     240

TGGTTGGACT TCAGCCCTCC GAAGTGCCTC CCACAACGGT TGTGAAGTTC CTGGGGCCG      300

GCACTGCGGC CTGTTTTGCG GACCTCCTCA CTTTTCCCCT GGACACCGCC AAGGTCCGTC     360

TGCAGATCCA AGGGGAGAAC CCAGGGGCTC AGAGCGTGCA GTACCGCGGT GTGCTGGGTA     420

CCATCCTGAC TATGGTGCGC ACAGAGGGTC CCCGCAGCCC TACAGCGGA CTGGTCGCTG      480

GCCTGCACCG CCAGATGAGT TTTGCCTCCA TTCGAATTGG CCTCTACGAC TCTGTCAAGC     540

AGTTCTACAC CCCCAAGGGA GCGGACCACT CCAGCGTCGC CATCAGGATT CTGGCAGGCT     600

GCACGACAGG AGCCATGGCA GTGACCTGCG CCCAGCCCAC GGATGTGGTG AAGGTCCGAT     660

TTCAAGCCAT GATACGCCTG GGAACTGGAG GAGAGAGGAA ATACAGAGGG ACTATGGATG     720

CCTACAGAAC CATCGCCAGG GAGGAAGGAG TCAGGGGCCT GTGGAAAGGG ACTTGGCCCA     780

ACATCACAAG AAATGCCATT GTCAACTGTG CTGAGATGGT GACCTACGAC ATCATCAAGG     840

AGAAGTTGCT GGAGTCTCAC CTGTTTACTG ACAACTTCCC CTGTCACTTT GTCTCTGCCT     900

TTGGAGCTGG CTTCTGTGCC ACAGTGGTGG CCTCCCCGGT GGATGTGGTA AAGACCCGAT     960

ACATGAACGC TCCCCTAGGC AGGTACCGCA GCCCTCTGCA CTGTATGCTG AAGATGGCGG    1020

CTCAGGAGGG ACCCACGGCC TTCTACAAAG GATTTGTGCC CTCCTTTCTG CGTCTGGGAG    1080

CTTGGAACGT GATGATGTTT GTAACATATG AGCAACTGAA GAGGGCCTTA ATGAAAGTCC    1140

AGGTACTGCG GGAATCTCCG TTTTGAACAA GGCAAGCAGG CTGCCTGAAA CAGAACAAAG    1200

CGTCTCTGCC CTGGGACACA AGGCCCACAC GGTCCAAAAC CCTGCACTGC TGCTGACACG    1260

AGAAACTGAA CTAAAAGAGG AGAGTTTTAG TCCTCCGTGT TTCGTCCTAA AACACCTCTG    1320

TTTTGCACTG ACCTGATGGG AAATAAATTA TATTAATTTT TAAACCCCTT CCGGTTGGAT    1380

GCCTAATATT TAGGCAAGAG ACAACAAAGA AAACCAGAGT CAACTCCCTT GAAATGTAGG    1440

AATAAAGGAT GCATAATAAA CAGGAAAGGC ACAGGTTTTG AGAAGATCAG CCCACAGTGT    1500

TGTCCTTGAA TCAAACAAAA TGGTCGGAGG AACCCTTCGG CTTCAGCACA AGAGGTGAC     1560

TACAGCCTTC TGGTCACCAG ATGACTCCGC CCCTCTGTAA TGAGTCTGCC AAGTAGACTC    1620

TATCAAGATT CTGGGGAAAG GAGAAAGAAC ACATTGATAC TGCACAAATG AGTGGTGCTG    1680

GGCCCACCGA GGACACTGGA GGATGGAGCG TGATCTGGGA TAACAGTCCT TCTCTGTCTG    1740

CCTCATCAGG GTGTTGGGAA GATAGAAAGC GAAGCAGACA TGGAAGCACT TCCTAACAAG    1800

GCCTGTCATC GTCATCATCT ACAAATGTAA GCCTGAGGAC AATGTTTTAG GAGAGATTCT    1860

GTCCAGAGAA GTAGTTTGAG GAAAATGCAG TTTGTAGTGG TAAAGCCATG CACACCTGGA    1920

CTGCATGGTA AGGACCAGGG GTGACGGAAG CCATGGGGAT CCGGTGCCTG GTAACATCAA    1980

AGGGCTGTGG GGGGGGGGG GCACTGCCTG TCCATCAGTT CAAAGCAGCA GGACTCAGAA     2040

TCTCCACCTT AGGGCAAGAA CGAGAACAGC TGCTCTTCTG CCTTCTCTCT CGGAGGTTTT    2100

CTCATCTCAG GGTCCTACCT GCCAGGCTCC TGACCAGCTC CACCTGCCCA CACTTCCTCC    2160

TGCTCTCGCT GCCTTTGGCT GCAGAGCCTT TGCTCCTCCT GTTAAGCCTT CAGTCTTCCA    2220

TCTGCAAAAG GGAGGGCAAA GCACAGGACC AACTTCCAAG CTTAAAAATG CACATCTGAC    2280

AACAAAATGG CTCAGTGGGG TCCATTCATG GGACCCACAT GGTGGAAGGA CAGAATGGAC    2340

TCTTGCAAAT TGTCCTCTGA CCTCCATTTG AGCGCCCTAT ACATGTGACT GTACATATGT    2400
```

-continued

```
ACAAACACGA TAAAGATGGA AACACATGTA AAAACATAAA AATAAAAAGT TGTACTGGAT    2460

GTGGTGGTTT GAATGAGATG TTCCTCGTGT CTCGGGCATT TGAAGACTTG CTCCCCAGTT    2520

GTTGGCGGCT GTTTGGGGAG GCTTAGAAGA TGTGGCCTTT TGGGAAGCAG GGTGTCATTG    2580

AGGACTGGCT TGGAGAGCCT AAAGATCCGA GGCACTCCCA GTTTCTCTGG TTTTTCATTT    2640

TGAGGTGTGA GGTCTTATTG GCTGCACCAG TCTCCATGCC TGTCTGTTGC CCGGCCTCCT    2700

CACCATGATG GACTTTTATC TCTCTGTACT TGTAAGCCCC AAATAAACCT TCCATCTGTG    2760

AAAAAAAAAA AAAAAAAAAA AA                                             2782
```

(2) INFORMATION FOR SEQ ID NO:2:

(i) SEQUENCE CHARACTERISTICS:
        (A) LENGTH: 308 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Val Gly Leu Gln Pro Ser Glu Val Pro Pro Thr Thr Val Val Lys
 1               5                  10                  15

Phe Leu Gly Ala Gly Thr Ala Ala Cys Phe Ala Asp Leu Leu Thr Phe
                20                  25                  30

Pro Leu Asp Thr Ala Lys Val Arg Leu Gln Ile Gln Gly Glu Asn Pro
            35                  40                  45

Gly Ala Gln Ser Val Gln Tyr Arg Gly Val Leu Gly Thr Ile Leu Thr
    50                  55                  60

Met Val Arg Thr Glu Gly Pro Arg Ser Pro Tyr Ser Gly Leu Val Ala
65                  70                  75                  80

Gly Leu His Arg Gln Met Ser Phe Ala Ser Ile Arg Ile Gly Leu Tyr
                85                  90                  95

Asp Ser Val Lys Gln Phe Tyr Thr Pro Lys Gly Ala Asp His Ser Ser
            100                 105                 110

Val Ala Ile Arg Ile Leu Ala Gly Cys Thr Thr Gly Ala Met Ala Val
        115                 120                 125

Thr Cys Ala Gln Pro Thr Asp Val Val Lys Val Arg Phe Gln Ala Met
    130                 135                 140

Ile Arg Leu Gly Thr Gly Gly Glu Arg Lys Tyr Arg Gly Thr Met Asp
145                 150                 155                 160

Ala Tyr Arg Thr Ile Ala Arg Glu Glu Gly Val Arg Gly Leu Trp Lys
                165                 170                 175

Gly Thr Trp Pro Asn Ile Thr Arg Asn Ala Ile Val Asn Cys Ala Glu
            180                 185                 190

Met Val Thr Tyr Asp Ile Ile Lys Glu Lys Leu Leu Glu Ser His Leu
        195                 200                 205

Phe Thr Asp Asn Phe Pro Cys His Phe Val Ser Ala Phe Gly Ala Gly
    210                 215                 220

Phe Cys Ala Thr Val Val Ala Ser Pro Val Asp Val Val Lys Thr Arg
225                 230                 235                 240

Tyr Met Asn Ala Pro Leu Gly Arg Tyr Arg Ser Pro Leu His Cys Met
                245                 250                 255

Leu Lys Met Ala Ala Gln Glu Gly Pro Thr Ala Phe Tyr Lys Gly Phe
            260                 265                 270

Val Pro Ser Phe Leu Arg Leu Gly Ala Trp Asn Val Met Met Phe Val
        275                 280                 285
```

Thr Tyr Glu Gln Leu Lys Arg Ala Leu Met Lys Val Gln Val Leu Arg
    290                 295                 300

Glu Ser Pro Phe
305

(2) INFORMATION FOR SEQ ID NO:3:

(i) SEQUENCE CHARACTERISTICS:
        (A) LENGTH: 1949 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| GTCAGCTGGT | GCACAGGGCC | AGTGCCGAGC | CAGGGACAGC | AGAGACAACA | GTGAATGGTG | 60 |
| AGGCCCGGCC | GTCAGATCCT | GCTGCTACCT | AATGGAGTGG | AGCCTTAGGG | TGGCCCTGCA | 120 |
| CTACCCAACC | TTGGCTAGAC | GCACAGCTTC | CTCCCTGAAC | TGAAGCAAAA | GATTGCCAGG | 180 |
| CAAGCTCTCT | CCTCGGACCT | CCATAGGCAG | CAAAGGAACC | AGGCCCATTC | CCCGGGACCA | 240 |
| TGGTTGGACT | TCAGCCCTCC | GAAGTGCCTC | CCACAACGGT | TGTGAAGTTC | CTGGGGGCCG | 300 |
| GCACTGCGGC | CTGTTTTGCG | GACCTCCTCA | CTTTTCCCCT | GGACACCGCC | AAGGTCCGTC | 360 |
| TGCAGATCCA | AGGGGAGAAC | CCAGGGGCTC | AGAGCGTGCA | GTACCGCGGT | GTGCTGGGTA | 420 |
| CCATCCTGAC | TATGGTGCGC | ACAGAGGGTC | CCCGCAGCCC | CTACAGCGGA | CTGGTCGCTG | 480 |
| GCCTGCACCG | CCAGATGAGT | TTTGCCTCCA | TTCGAATTGG | CCTCTACGAC | TCTGTCAAGC | 540 |
| AGTTCTACAC | CCCCAAGGGA | GCGGACCACT | CCAGCGTCGC | CATCAGGATT | CTGGCAGGCT | 600 |
| GCACGACAGG | AGCCATGGCA | GTGACCTGCG | CCCAGCCCAC | GGATGTGGTG | AAGGTCCGAT | 660 |
| TTCAAGCCAT | GATACGCCTG | GGAACTGGAG | GAGAGAGGAA | ATACAGAGGG | ACTATGGATG | 720 |
| CCTACAGAAC | CATCGCCAGG | GAGGAAGGAG | TCAGGGGCCT | GTGGAAAGGG | ACTTGGCCCA | 780 |
| ACATCACAAG | AAATGCCATT | GTCAACTGTG | CTGAGATGGT | GACCTACGAC | ATCATCAAGG | 840 |
| AGAAGTTGCT | GGAGTCTCAC | CTGTTTACTG | ACAACTTCCC | CTGTCACTTT | GTCTCTGCCT | 900 |
| TTGGAGCTGG | CTTCTGTGCC | ACAGTGGTGG | CCTCCCCGGT | GGATGTGGTA | AAGACCCGAT | 960 |
| ACATGAACGC | TCCCCTAGGC | AGGTACCGCA | GCCCTCTGCA | CTGTATGCTG | AAGATGGTGG | 1020 |
| CTCAGGAGGG | ACCCACGGCC | TTCTACAAAG | GATTTGTGCC | CTCCTTTCTG | CGTCTGGGAG | 1080 |
| CTTGGAACGT | GATGATGTTT | GTAACATATG | AGCAACTGAA | GAGGGCCTTA | ATGAAAGTCC | 1140 |
| AGGGTGTTGG | GAAGATAGAA | AGCGAAGCAG | ACATGGAAGC | ACTTCCTAAC | AAGGCCTGTC | 1200 |
| ATCGTCATCA | TCTACAAATG | GCAAGAACGA | GAACAGCTGC | TCTTCTGCCC | TCTCTCTCGG | 1260 |
| AGGTTTTCTC | ATCTCAGGGT | CCTACCTGCC | AGGCTCCTGA | CCAGCTCCAC | CTGCCCACAC | 1320 |
| TTCCTCCTGC | TCTCGCTGCC | TTTGGCTGCA | GAGCCTTTGC | TCCTCCTGTT | AAGCCTTCAG | 1380 |
| TCTTCCATCT | GCAAAAGGGA | GGGCAAAGCA | CAGGACCAAC | TTCCAAGCTT | AAAAATGCAC | 1440 |
| ATCTGACAAC | AAAATGGCTC | AGTGGGGTCC | ATTCATGGGA | CCCACATGGT | GGAAGGACAG | 1500 |
| AATGGACTCT | TGCAAATTGT | CCTCTGACCT | CCATTTGAGC | GCCCTATACA | TGTGACTGTA | 1560 |
| CATATGTACA | AACACGATAA | AGATGGAAAC | ACATGTAAAA | ACATAAAAAT | AAAAAGTTGT | 1620 |
| ACTGGATGTG | GTGGTTTGAA | TGAGATGTTC | CTCGTGTCTC | GGGCATTTGA | AGACTTGCTC | 1680 |
| CCCAGTTGTT | GGCGGCTGTT | TGGGGAGGCT | TAGAAGATGT | GGCCTTTTGG | GAAGCAGGGT | 1740 |
| GTCATTGAGG | ACTGGCTTGG | AGAGCCTAAA | GATCCGAGGC | ACTCCCAGTT | TCTCTGGTTT | 1800 |

TTCATTTTGA GGTGTGAGGT CTTATTGGCT GCACCAGTCT CCATGCCTGT CTGTTGCCCG    1860

GCCTCCTCAC CATGATGGAC TTTTATCTCT CTGTACTTGT AAGCCCCAAA TAAACCTTCC    1920

ATCTGTGAAA AAAAAAAAAA AAAAAAAA    1949

(2) INFORMATION FOR SEQ ID NO:4:

(i) SEQUENCE CHARACTERISTICS:
        (A) LENGTH: 432 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Val Gly Leu Gln Pro Ser Glu Val Pro Pro Thr Thr Val Val Lys
  1               5                  10                  15

Phe Leu Gly Ala Gly Thr Ala Ala Cys Phe Ala Asp Leu Leu Thr Phe
             20                  25                  30

Pro Leu Asp Thr Ala Lys Val Arg Leu Gln Ile Gln Gly Glu Asn Pro
         35                  40                  45

Gly Ala Gln Ser Val Gln Tyr Arg Gly Val Leu Gly Thr Ile Leu Thr
 50                  55                  60

Met Val Arg Thr Glu Gly Pro Arg Ser Pro Tyr Ser Gly Leu Val Ala
 65                  70                  75                  80

Gly Leu His Arg Gln Met Ser Phe Ala Ser Ile Arg Ile Gly Leu Tyr
                 85                  90                  95

Asp Ser Val Lys Gln Phe Tyr Thr Pro Lys Gly Ala Asp His Ser Ser
                100                 105                 110

Val Ala Ile Arg Ile Leu Ala Gly Cys Thr Thr Gly Ala Met Ala Val
            115                 120                 125

Thr Cys Ala Gln Pro Thr Asp Val Val Lys Val Arg Phe Gln Ala Met
130                 135                 140

Ile Arg Leu Gly Thr Gly Gly Glu Arg Lys Tyr Arg Gly Thr Met Asp
145                 150                 155                 160

Ala Tyr Arg Thr Ile Ala Arg Glu Glu Gly Val Arg Gly Leu Trp Lys
                165                 170                 175

Gly Thr Trp Pro Asn Ile Thr Arg Asn Ala Ile Val Asn Cys Ala Glu
                180                 185                 190

Met Val Thr Tyr Asp Ile Ile Lys Glu Lys Leu Leu Glu Ser His Leu
            195                 200                 205

Phe Thr Asp Asn Phe Pro Cys His Phe Val Ser Ala Phe Gly Ala Gly
210                 215                 220

Phe Cys Ala Thr Val Val Ala Ser Pro Val Asp Val Val Lys Thr Arg
225                 230                 235                 240

Tyr Met Asn Ala Pro Leu Gly Arg Tyr Arg Ser Pro Leu His Cys Met
                245                 250                 255

Leu Lys Met Val Ala Gln Glu Gly Pro Thr Ala Phe Tyr Lys Gly Phe
            260                 265                 270

Val Pro Ser Phe Leu Arg Leu Gly Ala Trp Asn Val Met Met Phe Val
        275                 280                 285

Thr Tyr Glu Gln Leu Lys Arg Ala Leu Met Lys Val Gln Gly Val Gly
290                 295                 300

Lys Ile Glu Ser Glu Ala Asp Met Glu Ala Leu Pro Asn Lys Ala Cys
305                 310                 315                 320
```

```
His Arg His His Leu Gln Met Ala Arg Thr Arg Thr Ala Ala Leu Leu
                325                 330                 335

Pro Ser Leu Ser Glu Val Phe Ser Ser Gln Gly Pro Thr Cys Gln Ala
                340                 345                 350

Pro Asp Gln Leu His Leu Pro Thr Leu Pro Pro Ala Leu Ala Ala Phe
                355                 360                 365

Gly Cys Arg Ala Phe Ala Pro Pro Val Lys Pro Ser Val Phe His Leu
    370                 375                 380

Gln Lys Gly Gly Gln Ser Thr Gly Pro Thr Ser Lys Leu Lys Asn Ala
385                 390                 395                 400

His Leu Thr Thr Lys Trp Leu Ser Gly Val His Ser Trp Asp Pro His
                405                 410                 415

Gly Gly Arg Thr Glu Trp Thr Leu Ala Asn Cys Pro Leu Thr Ser Ile
                420                 425                 430

(2) INFORMATION FOR SEQ ID NO:5:

(i) SEQUENCE CHARACTERISTICS:
        (A) LENGTH: 1777 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GTCAGCTGGT GCACAGGGCC AGTGCCGAGC CAGGGACAGC AGAGACAACA GTGAATGGTG      60

AGGCCCGGCC GTCAGATCCT GCTGCTACCT AATGGAGTGG AGCCTTAGGG TGGCCCTGCA     120

CTACCCAACC TTGGCTAGAC GCACAGCTTC CTCCCTGAAC TGAAGCAAAA GATTGCCAGG     180

CAAGCTCTCT CCTCGGACCT CCATAGGCAG CAAAGGAACC AGGCCCATTC CCCGGGACCA     240

TGGTTGGACT TCAGCCCTCC GAAGTGCCTC CCACAACGGT TGTGAAGTTC CTGGGGGCCG     300

GCACTGCGGC CTGTTTTGCG GACCTCCTCA CTTTTCCCCT GGACACCGCC AAGGTCCGTC     360

TGCAGATCCA AGGGGAGAAC CCAGGGGCTC AGAGCGTGCA GTACCGCGGT GTGCTGGGTA     420

CCATCCTGAC TATGGTGCGC ACAGAGGGTC CCCGCAGCCC CTACAGCGGA CTGGTCGCTG     480

GCCTGCACCG CCAGATGAGT TTTGCCTCCA TTCGAATTGG CCTCTACGAC TCTGTCAAGC     540

AGTTCTACAC CCCCAAGGGA GCGGACCACT CCAGCGTCGC CATCAGGATT CTGGCAGGCT     600

GCACGACAGG AGCCATGGCA GTGACCTGCG CCCAGCCCAC GGATGTGGTG AAGGTCCGAT     660

TTCAAGCCAT GATACGCCTG GGAACTGGAG GAGAGAGGAA ATACAGAGGG ACTATGGATG     720

CCTACAGAAC CATCGCCAGG GAGGAAGGAG TCAGGGGCCT GTGGAAAGGG ACTTGGCCCA     780

ACATCACAAG AAATGCCATT GTCAACTGTG CTGAGATGGT GACCTACGAC ATCATCAAGG     840

AGAAGTTGCT GGAGTCTCAC CTGTTTACTG ACAACTTCCC CTGTCACTTT GTCTCTGCCT     900

TTGGAGCTGG CTTCTGTGCC ACAGTGGTGG CCTCCCCGGT GGATGTGGTA AGACCCGAT     960

ACATGAACGC TCCCCTAGGC AGGTACCGCA GCAGGACTCA GAATCTTTAG GGAATTGTTA    1020

GGACTGGTAA AGAATTTCC ACCTTAGGGC AAGAACGAGA ACAGCTGCTC TTCTGCCTTC    1080

TCTCTCGGAG GTTTTCTCAT CTCAGGGTCC TACCTGCCAG GCTCCTGACC AGCTCCACCT    1140

GCCCACACTT CCTCCTGCTC TCGCTGCCTT TGGCTGCAGA GCCTTTGCTC CTCCTGTTAA    1200

GCCTTCAGTC TTCCATCTGC AAAAGGGAGG GCAAAGCACA GGACCAACTT CCAAGCTTAA    1260
```

-continued

```
AAATGCACAT CTGACAACAA AATGGCTCAG TGGGGTCCAT TCATGGGACC CACATGGTGG        1320

AAGGACAGAA TGGACTCTTG CAAATTGTCC TCTGACCTCC ATTTGAGCGC CCTATACATG        1380

TGACTGTACA TATGTACAAA CACGATAAAG ATGGAAACAC ATGTAAAAAC ATAAAAATAA        1440

AAAGTTGTAC TGGATGTGGT GGTTTGAATG AGATGTTCCT CGTGTCTCGG GCATTTGAAG        1500

ACTTGCTCCC CAGTTGTTGG CGGCTGTTTG GGGAGGCTTA AAGATGTGG CCTTTTGGGA         1560

AGCAGGGTGT CATTGAGGAC TGGCTTGGAG AGCCTAAAGA TCCGAGGCAC TCCCAGTTTC        1620

TCTGGTTTTT CATTTTGAGG TGTGAGGTCT TATTGGCTGC ACCAGTCTCC ATGCCTGTCT        1680

GTTGCCCGGC CTCCTCACCA TGATGGACTT TTATCTCTCT GTACTTGTAA GCCCCAAATA        1740

AACCTTCCAT CTGTGAAAAA AAAAAAAAAA AAAAAA                                  1777
```

(2) INFORMATION FOR SEQ ID NO:6:

(i) SEQUENCE CHARACTERISTICS:
        (A) LENGTH: 256 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Val Gly Leu Gln Pro Ser Glu Val Pro Thr Thr Val Val Lys
 1               5                  10                  15

Phe Leu Gly Ala Gly Thr Ala Ala Cys Phe Ala Asp Leu Leu Thr Phe
                20                  25                  30

Pro Leu Asp Thr Ala Lys Val Arg Leu Gln Ile Gln Gly Glu Asn Pro
                35                  40                  45

Gly Ala Gln Ser Val Gln Tyr Arg Gly Val Leu Gly Thr Ile Leu Thr
     50                  55                  60

Met Val Arg Thr Glu Gly Pro Arg Ser Pro Tyr Ser Gly Leu Val Ala
65                  70                  75                  80

Gly Leu His Arg Gln Met Ser Phe Ala Ser Ile Arg Ile Gly Leu Tyr
                85                  90                  95

Asp Ser Val Lys Gln Phe Tyr Thr Pro Lys Gly Ala Asp His Ser Ser
                100                 105                 110

Val Ala Ile Arg Ile Leu Ala Gly Cys Thr Thr Gly Ala Met Ala Val
                115                 120                 125

Thr Cys Ala Gln Pro Thr Asp Val Val Lys Val Arg Phe Gln Ala Met
        130                 135                 140

Ile Arg Leu Gly Thr Gly Gly Glu Arg Lys Tyr Arg Gly Thr Met Asp
145                 150                 155                 160

Ala Tyr Arg Thr Ile Ala Arg Glu Glu Gly Val Arg Gly Leu Trp Lys
                165                 170                 175

Gly Thr Trp Pro Asn Ile Thr Arg Asn Ala Ile Val Asn Cys Ala Glu
                180                 185                 190

Met Val Thr Tyr Asp Ile Ile Lys Glu Lys Leu Leu Glu Ser His Leu
                195                 200                 205

Phe Thr Asp Asn Phe Pro Cys His Phe Val Ser Ala Phe Gly Ala Gly
        210                 215                 220

Phe Cys Ala Thr Val Val Ala Ser Pro Val Asp Val Val Lys Thr Arg
225                 230                 235                 240

Tyr Met Asn Ala Pro Leu Gly Tyr Arg Ser Arg Thr Gln Asn Leu
                245                 250                 255
```